United States Patent [19]

Faschingleitner et al.

[11] Patent Number: 4,737,652

[45] Date of Patent: Apr. 12, 1988

[54] METHOD FOR THE PERIODIC DETERMINATION OF A QUANTITY TO BE MEASURED, USING A REFERENCE SIGNAL

[75] Inventors: Leopold Faschingleitner, Mank; Peter W. Krempl; Wolfgang Schindler, both of Graz, all of Austria

[73] Assignee: A V L Gesellschaft fur Verbrennungskraftmaschinen und Messtechnik M.B. Prof. Dr. Dr.h.c. Hans List, Graz, Austria

[21] Appl. No.: 847,454

[22] Filed: Apr. 3, 1986

[30] Foreign Application Priority Data

Apr. 4, 1985 [AT] Austria .................................. 1028/85

[51] Int. Cl.[4] .......................................... G01N 21/49
[52] U.S. Cl. ..................................... 250/575; 356/341
[58] Field of Search ............... 250/573, 575; 340/628; 356/341, 342, 437

[56] References Cited

U.S. PATENT DOCUMENTS 3,489,906  1/1970  Beer ..................................... 250/575
3,988,591 10/1976  Killer ................................... 250/575
4,001,595  1/1977  Reisman .............................. 250/575

FOREIGN PATENT DOCUMENTS 376301 11/1984 Austria .
2154611  5/1973 Fed. Rep. of Germany ...... 250/575

Primary Examiner—David C. Nelms
Assistant Examiner—Stephone B. Allen
Attorney, Agent, or Firm—Watson, Cole, et al.

[57] ABSTRACT

In order to eliminate equipment-generated fluctuations during the periodic determination of a quantity to be measured which is effected by forming the difference between a measuring signal which has been altered relative to a source signal by the measurement variable and a reference signal which has remained unaffected relative to the source signal by the measurement variable, a base signal level is determined for each measuring cycle as the difference between the reference level and a zero level in the absence of a source signal, subsequent to which each actual reference signal level and each measuring signal level is compensated with the previously determined reference signal level. By amplifying the compensated reference signals prior to difference formation and standardizing the signal difference to the base signal level, a high degree of accuracy may be achieved even if the attenuations of the measuring signal caused by the quantity to be measured are very small.

12 Claims, 2 Drawing Sheets

METHOD FOR THE PERIODIC DETERMINATION OF A QUANTITY TO BE MEASURED, USING A REFERENCE SIGNAL

BACKGROUND OF THE INVENTION

This inventions relates to a method for the periodic determination of a quantity to be measured, above all for the continuous measurement of the mass of aerosol particles in gaseous samples, each determination of the measurement value involving the measuring of at least one measuring signal which differs from the source signal due to the influence of the quantity to be measured, and of at least one reference signal which is not subject to the influence of the quantity to be measured, after which the difference between the two signals is formed and the value of the quantity to be measured is inferred from this difference, and to a device for implementation of this method.

DESCRIPTION OF THE PRIOR ART

Such methods and devices are known in various contexts; for example, AT-PS No. 376 301 describes a method of this kind for the continuous measuring of the mass of aerosol particles in gaseous samples, above all in the exhaust gas of internal combustion engines, in which both a test volume containing the sample and a reference volume are traversed by electromagnetic radiation of a given wavelength, the difference in radiation intensity after passage through the two volumes corresponding to the value of the measurement variable to be determined.

This method has certain disadvantages; for instance, if the difference between the reference signal and the measurement signal from which the value of the measurement variable is inferred, is very small, the fluctuations of the difference signal to be utilized in the periodic determination of the quantity to be measured will be even smaller and may be of the order of magnitude of equipment-generated fluctuations, e.g. of the intensity of the source signal or the efficiency of a detector, which will render impossible any meaningful and accurate measurement and could also lead to an overload in the amplifiers for the difference signal.

In the above example of measuring the content of aerosol particles in the exhaust gas of an internal combustion engine absorptions of less than 1% must be expected if particle concentrations of 1 mg/m$^3$ and less are to be measured, which—in view of the fact that both source intensity of the source signal and detector sensitivity may be subject to fluctuations of up to 10%—will make it difficult to perform accurate and significant measurements.

SUMMARY OF THE INVENTION

It is an object of the present invention to improve a method of the aforementioned type, and a device for implementation of this method, in such a way that even small changes in the quantity to be measured may be detected in an accurate and significant manner, i.e. largely independent of equipment-generated fluctuations.

According to the invention this is achieved as follows: (a) for each determination of the measurement value a base signal level is determined as the difference between the reference signal level and a zero level in the absence of the source signal; (b) the actual reference signal level is determined once again and is compensated with the previously measured reference signal level; (c) the measuring signal level is determined and is also compensated with the previously measured reference signal level; (d) the reference signal and the measuring signal compensated in this manner are amplified to the same extent; (e) the difference of the amplified and compensated signals is formed; (f) this difference is used for inferring the measurement value taking into account the base signal level. As the base signal level is determined for each individual measuring cycle fluctuations in the source signal which are caused by the equipment rather than by the quantity to be measured, i.e. fluctuations in source intensity, are prevented from influencing the respective determination of the quantity to be measured; in the same way the determination of the zero level will eliminate the influence of fluctuations in detection sensitivity.

The actual reference signal level used for measuring purposes which, in ideal circumstances, i.e. without the equipment-generated fluctuations mentioned above, should be equal to the previously determined reference signal level, is compensated with the previously determined reference signal level in the same way as the measuring signal level which has been altered by the quantity to be measured, such that compensated signals are obtained relative to the respective actual intensity of the source signal. After the signals have been amplified in order to increase accuracy, the difference of the amplified and compensated signals is formed from which the measured value is inferred, taking into account the base signal level described above.

In this manner equipment-generated fluctuations can be taken into account and significant measurements may be performed even if the signal differences are very small.

In a further development of the invention the base signal level is taken into account by dividing the difference of the compensated and amplified signals by the base signal level, and by inferring the quantity to be measured from the signal standardised in this way. This is a very simple method of taking into account the fluctuating base signal level in the compensated and amplified difference signal, which may easily be realized from the point of view of equipment as well.

In a preferred form of the invention the degree of amplification of the compensated signals is at least approximately reciprocal to the degree of attenuation of the measuring signal relative to the source signal. In this way the difference of the compensated signals may be determined with similar accuracy as the base signal level which is a measure for the relevant intensity of the source signal; this will only be possible in connection with the above described dynamic compensation of the signals obtained for each measuring cycle, as without such compensation taking into account any equipment-generated fluctuations, or in the instance of dynamic compensation being replaced by fixed value compensation, the amplifier would be overloaded continuously.

In a device for implementation of the method described by the present invention for the purpose of absorption measurements in gaseous samples, comprising a radiation source, and a test volume containing the sample as well as a reference volume free of any substances to be detected, both of which are irradiated by the radiation source, and further comprising a detector which is fed via a selector unit with at least one measuring signal from the test volume and at least one reference signal from the reference volume, arriving in alternating order, and further comprising an evaluation unit connected to the detector, which is used for forming the difference of the respective signals and for inferring the quantity to be measured from it—which device is known, for instance, from the above mentioned publication AT-PS No. 376 301—another variant of the invention proposes that the evaluation unit be provided with an A/D converter for determining signal intensities which is connected to the detector via a compensation unit followed by an amplifier, and that a D/A converter be provided which is connected to the A/D converter via an intermediate memory and is used for generating a compensation voltage from the reference signal level obtained before, its output being connected with an input of the compensation unit, and, further, that the output of the A/D converter be connected to an input of a micro-processor of the evaluation unit. This is a very simple enhancement of the device for the periodic determination of a measurement variable by means of the method proposed here, which is suitable for high measuring frequencies and will ensure a high degree of measuring accuracy.

In order to avoid large signal amplitudes and to increase accuracy a further variant of the invention proposes a memory unit to be included between the output of the detector and the compensation unit, which will store the latest signal level while the selector unit is being switched.

In order to simplify the configuration of the entire device, above all that of the evaluation unit, which will reduce costs, another variant of the invention provides that the compensation unit, together with the amplifier by which it is followed, be configured as a programmable instrument amplifier.

In another preferred development of the invention the evaluation unit comprises a time sequence control unit which is connected to the selector unit and will supply control signals to the other components of the evaluation unit via output lines, in accordance with the respective position of the selector unit. This will permit in a simple way a precise synchronisation of the detection and processing of the individual signals.

DESCRIPTION OF THE DRAWINGS

Following is a more detailed description of the invention as illustrated by the accompanying drawings.

Figure 1:
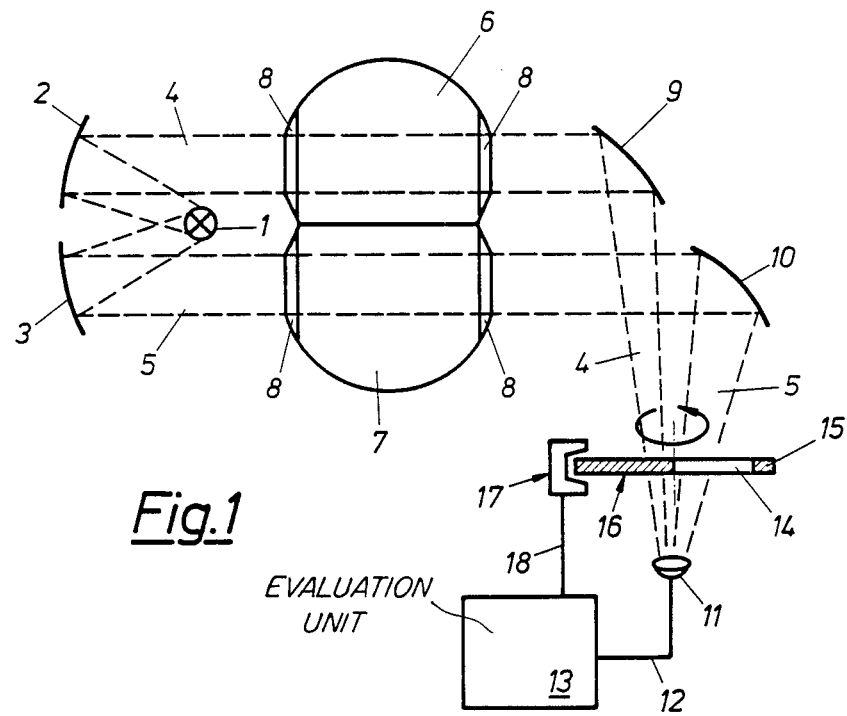
FIG. 1 shows a device for absorption measurements in gaseous samples as described by the invention.

The device of FIG. 1 is used for periodic measurings, for instance of the mass of aerosol particles in the exhaust gas of internal combustion engines. A radiation source 1 emits electromagnetic radiation in the infra-red range which, after reflection at two concave mirrors 2, 3, passes through a reference volume 6 and a test volume 7 in the form of two partial beams 4, 5 by means of radiation-transparent windows 8. After reflection at two further concave mirrors 9, 10 the partial beams 4, 5 are focussed onto a common detector 11 which is connected via a line 12 with an evaluation unit 13. In the beam path of the two partial beams 4, 5 in front of the detector 11 there is situated a selector unit 16 configured here as a chopper disk 15 provided with openings or filters 14, which unit, by the controlled revolution of the chopper disk 15, permits the passage towards the common detector 11 of the measuring signal (partial beam 5) coming from the test volume 7, and the reference signal (partial beam 4) coming from the reference volume 6, in a given time sequence and alternating order.

A light barrier 17 is connected via a line 18 to a time sequence control unit (not shown here) in the evaluation unit 13, which permits a precise synchronisation of the detection and processing of the individual signals, e.g. in connection with the trigger marks (cf. signals shown in track $T_1$ of FIG. 2) provided at the circumference of the chopper disk 15.

Based on the diagram in FIG. 2 the periodic determination of a measurement value in a device as shown in FIG. 1 will be described more closely below.

Figure 2:
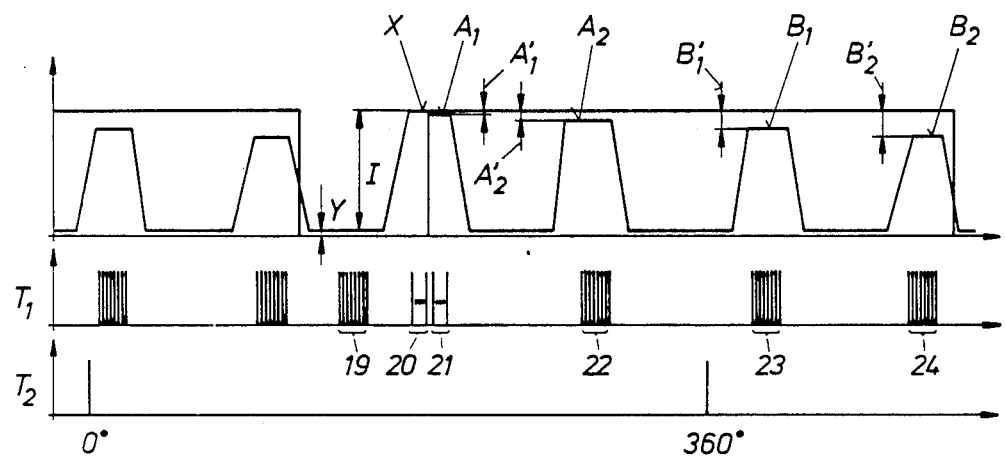
FIG. 2 shows a diagram with the waveform of the pre-amplified detector signal over time or over the rotation angle of the selector unit, as it is obtained with a device according to FIG. 1 and as it is used according to the invention for the periodic determination of the measurement value.

First of all it should be pointed out that the signal waveform shown in the topmost part of FIG. 2 corresponds to the detector signal delivered via line 12 which may already be pre-amplified or otherwise processed, four signal levels which are influenced in different ways by the quantity to be measured, being passed to the detector 11 during each measuring cycle, i.e. during each revolution of the chopper disk 15, which means that two filters or openings 14 are provided on the chopper disk which are separated by areas non-transparent for the radiation used. Apart from this it would also be possible, of course, to provide several openings/filters 14 on the chopper disk 15 in such a way that the partial beams 4, 5 are permitted to pass alternatingly. In any case two reference signal levels $A_1$ and $A_2$ at different wavelengths—produced by different filters 14—and two corresponding measuring signal levels $B_1$ and $B_2$ at the same wavelength are determined for each measuring cycle; the individual bars in part $T_1$ represent the individual recordings of the detector signal; in this instance each signal level is determined by eight individual measurements which are then averaged.

At the beginning of each measuring cycle a zero level Y is determined in the absence of a source signal—the respective individual measurements are denoted 19 in the trigger track $T_1$—after which a reference signal level X is determined by averaging the individual measurements 20, the selector unit 16 being in the same position as for determination of the subsequent actual reference signal level $A_1$.

From the reference signal level X and the zero level Y a base signal level $I = X - Y$ is obtained which will help take into account equipment-generated fluctuations when the final measurement value is determined. This will be further discussed later on.

In the area 21 of the trigger track $T_1$ the actual reference signal level $A_1$ is determined once more and is compensated with the previously determined reference signal level $X = I + Y$, which will yield a compensated reference signal $A_1'$, for instance as a consequence of filter densities varying in the individual areas. After this the other actual reference signal level $A_2$ is determined in area 22 of the trigger track $T_1$ and is also compensated with the previously determined reference signal level X, which will yield another compensated reference signal $A_2'$. For the sake of completeness it should be pointed out here that the reference signal levels $A_1$ and $A_2$ are obtained from the partial beam 4 in FIG. 1 which traverses the reference volume 6, containing a reference gas, e.g. pure air, such that these signals are not influenced relative to the source signal by the quantity to be measured.

In area 23 of the trigger track $T_1$ the measuring signal level $B_1$ is determined whose wavelength corresponds to that of the reference signal level $A_1$, or rather to the compensated reference signal $A_1'$, the level $B_1$ being characteristically attenuated by the quantity to be measured relative to the source signal due to the measuring of the partial beam 5 traversing the test volume. This signal level $B_1$ is again compensated with the previously determined reference signal X, which will yield the compensated measuring signal $B_1'$. In area 24 the second measuring signal level $B_2$ is determined corresponding to the reference signal level $A_2$ and/or the compensated reference signal level $A_2'$, and is again compensated with the previously determined reference signal level X, which will yield the compensated measuring signal $B_2'$. This marks the beginning of a new measuring cycle and signal recording begins once again; the first two signal peaks in FIG. 2, top left, are the levels of the previous cycle corresponding to the measuring signal levels $B_1$ and $B_2$.

For the sake of completeness the waveform of the compensation signal level should also be noted which is shown in the top section of FIG. 2 and corresponds to the previously measured reference signal level X, remaining constant over each full measuring cycle. The trigger track $T_2$ in FIG. 2 finally contains the angle marks 0° and 360° indicating the duration of a measuring cycle as defined by the revolution of the chopper disk 15.

In principle, the method may also be implemented with one single actual reference signal level A and one measuring signal level B for each measuring cycle; in the variant presented and discussed here two measuring values which are practically independent of each other—corresponding to differing absorptions at differing frequencies—are obtained for each measuring cycle, i.e. each revolution of the chopper disk 15.

The compensated reference signals $A_1'$, $A_2'$ and the compensated measuring signals $B_1'$, $B_2'$ are amplified to the same extent in the evaluation unit 13 (cf. FIG. 1), the degree of amplification being at least approximately reciprocal to the degree of attenuation of the measuring signals relative to the source signal in order to obtain difference signals with a degree of accuracy similar to that with which the base signal level I is determined. Finally, a difference $E_1 = A_1' - B_1'$ and $E_2 = A_2' - B_2'$ is formed in a manner not further illustrated here, which may be used for inferring the value of the quantity (or quantities) to be measured after the base signal level I has been taken into account, e.g. by dividing $E_1$ or $E_2$ by I.

As the previously measured reference signal level X used for compensation is kept constant over each measuring cycle—cf. FIG. 2—all reference values and measuring values of each measuring cycle are referred to the same level taking into account equipment-generated fluctuations, thus eliminating measurement errors due to such fluctuations and permitting highly accurate and significant measurings even if the signals are hardly attenuated by the quantity to be measured.

Figure 3:
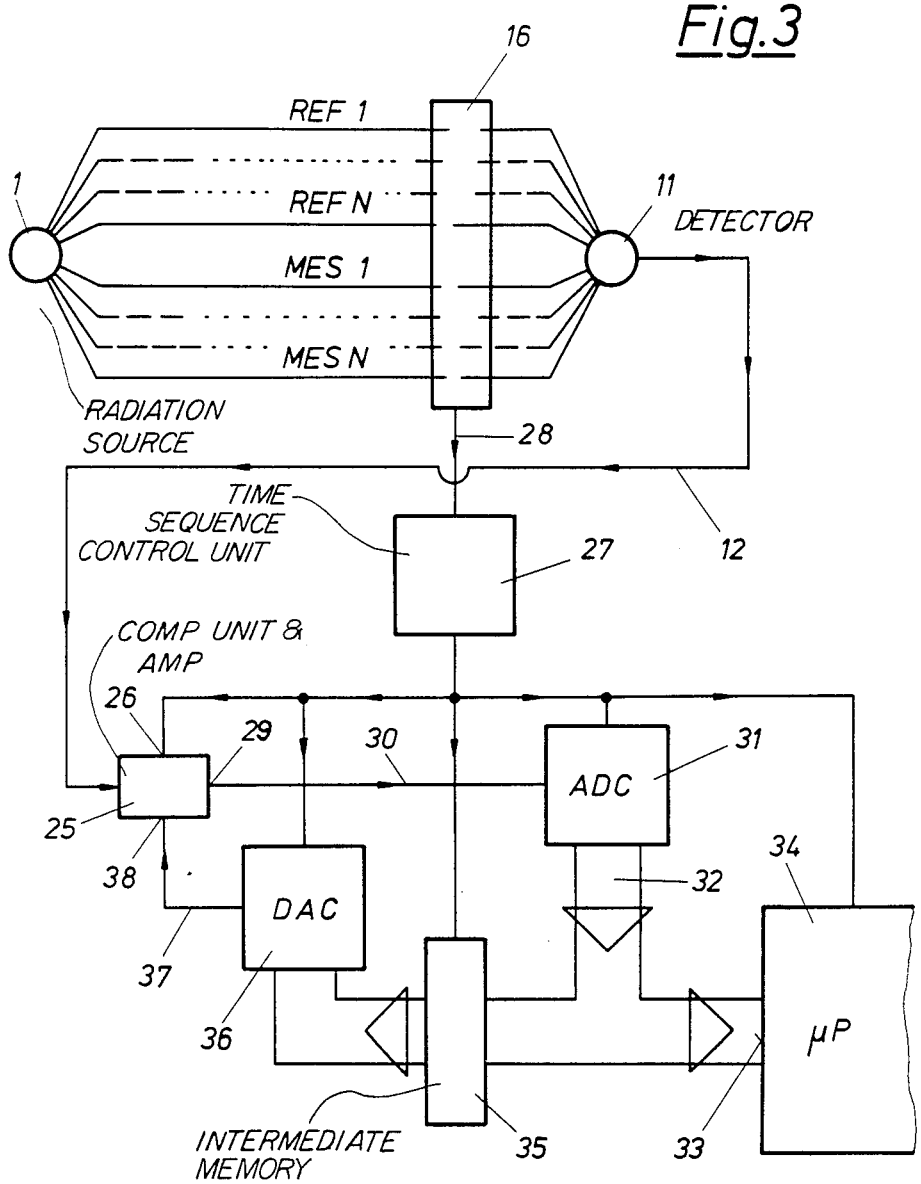
FIG. 3 presents another device according to the invention with a more detailed view of the evaluation unit.

In the device shown in FIG. 3 a single radiation source 1 and a single detector 11 are provided; the possible signal paths between the two are marked REF 1 to REF N for the unaffected reference signals, and MES 1 to MES N for the measuring signals which have been altered relative to the source signal by the quantity to be measured. In order to ensure that the possible paths are opened only one at a time a selector unit 16 is provided again, for which purpose any kind of multiplexer may be used.

Via line 12 the detector 11 is connected to a compensation unit followed by an amplifier—marked 25—which, via an input 26, is also connected to a time sequence control unit 27 receiving information on the actual position of the selector unit 16 via a line 28. The amplifier output 29 of the compensated unit 25 is connected to an A/D converter 31 by means of a line 30, which converter is used for determining and digitizing the respective signal intensities.

Via a data line 32 the A/D converter 31 is connected to the input 33 of a micro-processor 34 on the one hand and—via an intermediate memory 35—to a D/A converter 36 on the other hand which will generate a compensation voltage from the previously measured reference signal level (X in FIG. 2), the compensation voltage being applied via a line 37 to an input 38 of the compensation unit in unit 25.

Once again it should be pointed out for the sake of completeness that in addition to the unit 25 the two converters 31, 36 and the intermediate memory 35 and the micro-processor 34 are connected via respective lines to the time sequence control unit 27 which—in accordance with the actual position of the selector unit 16—will deliver control signals to these components for synchronization of signal detection and processing.

The unit 25 consisting of a compensation unit and an amplifier may be configured as a programmable instrument amplifier, for example, which will permit different degrees of amplification for the individual signals recorded (cf. description FIG. 2).

Between the output of detector 11 and the input of the compensation unit a memory unit (not shown here) could again be provided which would store the latest signal level during switching of the selector unit 16; in this way large signal amplitudes—as shown in FIG. 2—could be avoided and accuracy could be improved.

We claim:

1. A method for the periodic determination of a quantity to be measured, each determination of the measurement value involving the measuring of at least one measuring signal which differs from the source signal due to the influence of the quantity to be measured, and of at least one reference signal which is not subject to the influence of the quantity to be measured, after which the difference between the two signals is formed and the value of the quantity to be measured is inferred from said difference, comprising determining for each determination of the measurement value a base signal level (I) as the difference between the reference signal level (X) and a zero level (Y) in the absence of a source signal; again determining the actual reference signal level (A) and compensating the actual reference signal with the previously measured reference signal level ($x = I + Y$); determining the measuring signal level (B) and compensating the measuring signal level (B) with the previously measured reference signal level (X); amplifying the reference signal ($A' = A - X$) and the measuring signal ($B' = B - X$) compensated in this manner to substantially the same extent; forming the difference (E) of the amplified and compensated signals as ($E = A' - B'$); and inferring the measured value from said difference (E), taking into account the base signal level (I).

2. A method according to claim 1, wherein the base signal level (I) is taken into account by dividing the difference (E) of the compensated and amplified signals (A', B') by said base signal level (I), and by inferring the quantity to be measured from the signal standardised in this way (E'=E/I).

3. A method according to claim 1, wherein the degree of amplification of the compensated signals (A', B') is at least approximately reciprocal to the degree of attenuation of the measuring signal relative to the source signal.

4. A device for the periodic determination of a quantity to be measured from a sample, comprising a radiation source, and a test volume containing the sample, and a reference volume free of any substance to be detected, both of which volumes are irradiated by said radiation siurce, a detector fed via a selector unit with at least one measuring signal from said test volume and at least one reference signal from said reference volume, arriving in alternating order, an evaluation unit connected to said detector for forming the difference of the respective signals and for inferring the quantity to be measured from it, said evaluation unit including an A/D converter for determining signal intensities and connected to said detector via a compensation unit including an amplifier, a D/A converter connected to said A/D converter via an intermediate memory for generating a compensation voltage from the previously determined reference signal level (X), and having an output connected with an input of said compensation unit, and the output of said A/D converter being connected to an input of a micro-processor of said evaluation unit.

5. A device according to claim 4, wherein a memory unit is provided between the output of said detector and the input of said compensation unit, for storing the latest signal level while the selector unit is being switched.

6. A device according to claim 4, wherein the compensation unit including said amplifier is configured as a programmable instrument amplifier.

7. A device according to 4, wherein the evaluation unit comprises a time sequence control unit connected to said selector unit for supplying control signals to the other components of said evaluation unit via output lines, in accordance with the respective position of said selector unit.

8. A method according to claim 2, wherein the degree of amplification of the compensate signals (A', B',) is at least approximately reciprocal to the degree of attenuation of the measuring signal relative to the source signal.

9. A device according to claim 5, wherein the compensation unit including said amplifier is configured as a programmable instrument amplifier.

10. A device according to claim 5, wherein the evaluation unit comprises a time sequence control unit connected to said selector unit for supplying control signals to the other components of said evaluation unit via output lines, in accordance with the respective position of said selector unit.

11. A device according to claim 6, wherein the evaluation unit comprises a time sequence control unit connected to said selector unit for supplying control signals to the other components of said evaluation unit via output lines, in accordance with the respective position of said selector unit.

12. A device according to claim 9, wherein the evaluation unit comprises a time sequence control unit connected to said selector unit for supplying control signals to the other components of said evaluation unit via output lines, in a ccordance with the respective position of said selector unit.

* * * * *

UNITED STATES PATENT AND TRADEMARK OFFICE
CERTIFICATE OF CORRECTION

PATENT NO.    : 4,737,652
DATED         : April 12, 1988
INVENTOR(S)   : Faschingleitner et al It is certified that error appears in the above-identified patent and that said Letters Patent is hereby corrected as shown below:

On the Title Page:
Assignee's name should read as follows:

[73] Assignee: A V L Gesellschaft für Verbrennungskraftmaschinen und Messtechnik M.B.H. Prof.Dr.Dr.h.c. Hans List Signed and Sealed this Fifteenth Day of November, 1988

Attest:

DONALD J. QUIGG

*Attesting Officer*  *Commissioner of Patents and Trademarks*